(12) United States Patent
Wang et al.

(10) Patent No.: US 10,272,447 B2
(45) Date of Patent: Apr. 30, 2019

(54) SAMPLE CARRIER CENTRIFUGE

(71) Applicant: Yantai AusBio Laboratories Co., Ltd., Yeda, Yantai, Shandong (CN)

(72) Inventors: Zhaoqiang Wang, Yantai (CN); Friedrich Neuhäusser-Wespy, Zurich (CH)

(73) Assignee: Yantai AusBio Laboratories Co., Ltd., Yeda (CN)

( * ) Notice: Subject to any disclaimer, the term of this patent is extended or adjusted under 35 U.S.C. 154(b) by 378 days.

(21) Appl. No.: 14/376,690

(22) PCT Filed: Feb. 6, 2013

(86) PCT No.: PCT/EP2013/052356
§ 371 (c)(1),
(2) Date: Aug. 5, 2014

(87) PCT Pub. No.: WO2013/117606
PCT Pub. Date: Aug. 15, 2013

(65) Prior Publication Data
US 2015/0031521 A1    Jan. 29, 2015

(30) Foreign Application Priority Data
Feb. 6, 2012  (DE) .............. 10 2012 201 717

(51) Int. Cl.
*B04B 7/12* (2006.01)
*B04B 5/04* (2006.01)
(Continued)

(52) U.S. Cl.
CPC ............. *B04B 7/12* (2013.01); *B04B 5/0414* (2013.01); *B04B 5/10* (2013.01); *B04B 7/02* (2013.01);
(Continued)

(58) Field of Classification Search
CPC .... B04B 7/12; B04B 7/02; B04B 9/12; B04B 9/14; B04B 11/04; B04B 5/10;
(Continued)

(56) References Cited

U.S. PATENT DOCUMENTS 2,821,339 A * 1/1958 Wyble ...................... B04B 5/04
                                                        211/1.53
5,855,545 A * 1/1999 Kishi ........................ B04B 7/02
                                                        494/12
(Continued)

FOREIGN PATENT DOCUMENTS

DE        106482        6/1974
EP      0305337 A1      3/1989
(Continued)

OTHER PUBLICATIONS

International Preliminary Report on Patentability, dated Aug. 21, 2014, from counterpart International Application No. PCT/EP2013/052356, filed on Feb. 6, 2013.
(Continued)

*Primary Examiner* — Marc C Howell
(74) *Attorney, Agent, or Firm* — HoustonHogle LLP

(57) ABSTRACT

The invention relates to a sample carrier centrifuge for a sample carrier (24) that has at least one sample channel (26) extending along an essentially central sample channel longitudinal axis (P), having a sample carrier receptacle (14), which can be rotated around a rotation axis (R) and has a holding section (38) into which the sample carrier (24) can be inserted in a loading procedure when the sample carrier receptacle (14) is not rotating, in which section the sample carrier (24) is held in the loaded state of the sample carrier receptacle (14), and from which section the sample carrier (24) can be removed in an unloading procedure, which is characterized in that a platform (22) of the sample carrier centrifuge (10), which is embodied for supporting the
(Continued)

sample carrier centrifuge (10) in accordance with its designated use, is oriented parallel to the rotation axis (R).

27 Claims, 7 Drawing Sheets

(51) Int. Cl.
    *B04B 5/10*     (2006.01)
    *B04B 9/14*     (2006.01)
    *B04B 9/12*     (2006.01)
    *B04B 11/04*     (2006.01)
    *G01N 33/53*     (2006.01)
    *B04B 7/02*     (2006.01)

(52) U.S. Cl.
    CPC ............... *B04B 9/12* (2013.01); *B04B 9/14* (2013.01); *B04B 11/04* (2013.01); *G01N 33/53* (2013.01); *B04B 2011/046* (2013.01); *C12Q 2547/107* (2013.01)

(58) Field of Classification Search
    CPC . B04B 5/0414; B04B 2011/046; G01N 33/53; C12Q 2547/107
    USPC ............................ 494/17, 16, 37, 45
    See application file for complete search history.

(56) References Cited

U.S. PATENT DOCUMENTS 7,824,559 B2 * 11/2010 Dorian ............... A61M 1/3633
    210/360.1
2007/0284320 A1 * 12/2007 Menhennett .......... B04B 5/0428
    210/782
2008/0182742 A1 * 7/2008 Porte .................... B04B 5/0407
    494/7
2009/0215603 A1 * 8/2009 Baumann .............. B04B 5/005
    494/17
2009/0274348 A1 * 11/2009 Jakubowicz ....... G01N 33/5304
    382/128
2013/0078149 A1 * 3/2013 Holmes ................ B04B 5/0414
    422/72
2013/0288873 A1 * 10/2013 Barbee .................... B04B 13/00
    494/9

FOREIGN PATENT DOCUMENTS

| EP | 0849595 A1 | 6/1998 | |
|---|---|---|---|
| EP | 2124054 A1 | 11/2009 | |
| JP | 2007296456 A | * 11/2007 | |
| WO | 03047759 A1 | 6/2003 | |
| WO | WO 03047759 A1 | * 6/2003 | ........... B04B 5/0414 |

OTHER PUBLICATIONS

Search report for counterpart German Application No. 10 2012 201 717.8, filed on Feb. 6, 2012.

International Search Report dated May 14, 2013, from counterpart International Application No. PCT/EP2013/052356, filed on Feb. 6, 2013.

* cited by examiner

SAMPLE CARRIER CENTRIFUGE

RELATED APPLICATIONS

This application is a § 371 National Phase Application of International Application No. PCT/EP2013/052356, filed on Feb. 6, 2013, now International Publication No. WO 2013/117606 A1, published on Aug. 15, 2013, which International Application claims priority to German Application No. DE 102012201717.8, filed on Feb. 6, 2012, all of which are incorporated herein by reference in their entirety.

The present invention relates to a sample carrier centrifuge for a sample carrier that has at least one sample channel extending along an essentially central sample channel longitudinal axis, having a sample carrier receptacle, which can be rotated around a rotation axis and has a holding section into which the sample carrier can be inserted in a loading procedure when the sample carrier receptacle is not rotating, in which section the sample carrier is held in the loaded state of the sample carrier receptacle, and from which section the sample carrier can be removed in an unloading procedure.

Sample carrier centrifuges of this kind are generally known in laboratory technology. In particular, FIG. 6 of EP 2 124 054 A1 has disclosed a sample carrier centrifuge of this generic type, which in accordance with its designated use, is supported on a horizontally oriented platform and can be rotated around a vertical rotation axis, i.e. an axis oriented orthogonally to the platform of the sample carrier centrifuge.

This known sample carrier centrifuge has a central shaft essentially concentric to the rotation axis from which bars extend radially with an angular offset of 180° relative to the rotation axis. At the end of the bars, sample carriers can be attached to sample carrier receptacles, which are not specifically shown, in order to be rotated around the rotation axis in the above-described sample carrier centrifuge.

The angular offset of 180° of the two bars protruding from the central shaft at right angles to the rotation axis is based on the advantageous symmetrical mass distribution of the rotation apparatus, which minimizes an imbalance during rotation of the sample carrier centrifuge as much as possible.

In the known sample carrier centrifuge, it is desirable on the one hand to centrifuge more than one sample carrier at a time, which increases the efficiency of the known sample carrier centrifuge.

On the other hand, with the same angular velocity of the known sample carrier centrifuge, the protruding bars, whose longitudinal ends oriented away from the shaft are provided with the sample carrier receptacles, provide for a higher path velocity of the sample carrier apparatus around the rotation axis and therefore a greater centrifugal force acting on the respective sample carriers the longer the bars are.

In the sample carrier centrifuge known from EP 2 124 054 A1, it is also advantageous that each sample carrier receptacle, i.e. at each longitudinal end of a bar oriented away from the central shaft, a sample carrier can be accommodated so that the sample channel longitudinal axis of the at least one sample channel included in the sample carrier extends essentially orthogonally to the rotation axis and is therefore oriented in the direction of action of the centrifugal force. Consequently, from the outset, the sample carriers of the known sample carrier centrifuge are arranged so that they are optimally oriented for a centrifuging process, i.e. a test substance introduced at one longitudinal end of a sample channel of a sample carrier can be driven into the sample carriers along the sample channel longitudinal axis with the aid of the centrifugal force exerted during the centrifuging process.

In this case, the sample carrier can be any sample carrier with a sample channel embodied according to the above description. Preferably, however, it is conceived for so-called "gel cards" or "bead cassettes," each of which has a plurality of sample carriers arranged so that they are provided parallel to one another, with their sample carrier longitudinal axes extending essentially in a plane in a shared axial section of the sample carrier. Such "gel cards" are likewise known from EP 2 124 054 A1 and are shown in FIGS. 3 and 4 thereof.

Similar sample carriers for which the present invention is preferably conceived are also known from EP 0 849 595 A1 or EP 0 305 337 A1. Sample carriers of this kind are essentially used to test for evidence of antigens and/or antibodies through the use of agglutination reactions. This testing takes advantage of the fact that in the same amount of time and with the same amount of force acting on them, substances with different agglutination rates penetrate different distances into a reference substance, in particular a reference gel, contained in the sample channel. The driving force in this case is the centrifugal force generated by the sample carrier centrifuge.

In the known sample carrier centrifuge, a sample carrier can in fact already be arranged in the provided sample carrier receptacle in the same orientation as the centrifugal force that will later be exerted during the centrifuging process. However, until the beginning of the centrifuging process, a time interval of arbitrary length can elapse during which the sample carriers that have been prepared for the centrifuging process are subjected exclusively to the force of gravity, which is oriented orthogonal to the sample channel longitudinal axis and therefore orthogonal to the desired penetration direction of a test substance into the reference substance. This can have negative effects on the subsequent test result and its reliability.

The time interval between the placement of a sample carrier into the sample carrier receptacle of the known sample carrier centrifuge and the beginning of the centrifuging process can end up being prolonged particularly due to the fact that it is first necessary to equip all of a plurality of provided sample carrier receptacles with sample carriers before the known sample carrier centrifuge can be operated with the least amount of imbalance possible.

Frequently, however, it is of critical importance to quickly carry out tests on a sample carrier that has been prepared and is ready for testing. In these cases, it is important to centrifuge a sample carrier as quickly as possible after test-ready installation in order to obtain the most meaningful and/or reliable test result possible.

US 2008/0182742 A1 discloses a centrifuge comprising a plurality of centrifuge discs, each disk having an attachment portion for attaching a container containing a liquid to be centrifuged, a disc driver provided for rotating the discs and a disc engager/disengager for individually moving each of the discs into and out of contact with the disc driver. The discs are rotating around a horizontal axis. The containers containing the liquid to be centrifuged can comprise several vessels. These containers are arranged in the plane of the corresponding disc. If such a container comprises several reaction vessels, then these reaction vessels are all arranged in a direction perpendicular to the rotation axis.

JP 2007-296456 A discloses a centrifuge for centrifuging a large number of tubes. This centrifuge comprises a vertical rotation axis.

DD 106 482 relates to a centrifuge for rotating plate-type elements comprising a holding mechanism which provides a holding force which is proportional to the rotational speed.

Under the trade name "Hanlab Compact Benchtop Centrifuges Labmaster® ABC-CB200/ABC-CB200 R", centrifuges are available comprising a built-in auto-balancing mechanism for compensating the weight difference of probes.

The object of the present invention, therefore, is to modify the sample carrier centrifuge of this generic type so that compared to the prior art, it is possible to keep the time between the test-ready installation of a sample carrier and the end of its centrifuging process and better still, the end of the evaluation of the centrifuged result, small and to allow to centrifuge reliably a plurality of samples or a large amount of sample probe with the high quality and effectiveness.

The object is solved by a sample carrier centrifuge according to claim 1. Advantageous embodiments are defined in the corresponding subclaims.

According to the most general basic concept of the present invention, this object is attained by means of a sample carrier centrifuge of the type mentioned at the beginning whose platform, which is embodied for setting up the sample carrier centrifuge in accordance with its designated use, is oriented parallel to the rotation axis, and wherein a sample carrier receptacle is provided for holding one or more sample carriers and the one or more sample carriers are extending substantially parallel to the rotation axis.

When set up as intended, the sample carrier centrifuge rests on its platform, which is embodied and arranged for this purpose. As a rule, the platform is horizontally embodied since laboratory devices like the sample carrier centrifuges in question here are usually used on laboratory tables.

With the design of the sample carrier centrifuge according to the invention, it is thus basically possible to produce the sample carrier centrifuge so that it is ready for operation with its rotation axis oriented horizontally. Sample carrier centrifuges with horizontally oriented rotation axes do in fact have the disadvantage that the centrifugal forces they generate are intensified by the force of gravity in a region below the rotation axis and are reduced by the force of gravity in a region above the rotation axis and thus a rising force is exerted on the sample carriers as a rotation progresses, but this disadvantage can be reduced and is more than compensated for by the achievable advantages of a sample carrier processing that is as quick as possible.

The disadvantages can be reduced, for example, by increasing the rotation speed. At speeds of greater than 3000 revolutions per minute, even with only a slight radial distance of the sample carrier from the rotation axis, it is possible to achieve centrifugal accelerations that are more than 100 times, actually more than 140 times the acceleration of gravity. In this case, the acceleration of gravity that acts in a different direction from the centrifugal force is an interference variable with an influence of less than 1%.

With the sample carrier centrifuge according to the invention, not only can a sample carrier be centrifuged particularly quickly after the test-ready introduction of the test substance, the sample carrier centrifuge can also be embodied as very small.

A sample carrier centrifuge having a platform parallel to the rotation axis is easily to implement into an automatic liquid handling system, because the sample carrier can be held in its regular position during loading the centrifuge with the sample carrier or discharging the centrifuge from the sample carrier.

The sample carrier can be any vessel for holding a liquid. Such a sample carrier can be a vessel having one or more unclosed openings such as a tube or microtiter plate. The regular position of the vessels with unclosed openings for carrying liquid samples is with the opening directed upwards so that the liquid sample is kept safely in the vessel.

The sample carrier can be also a completely closed or sealed sample. A blood bag is usually completely sealed. Tubes can be sealed by means of a lid. However, the opening and closing of tubes with a lid is difficult to carry out automatically.

Examples for suitable sample carriers are sample carriers having a sample channel, tubes, bottles, microtiter plates, blood bags, one or more tubes placed in a rack, carriers for taking up any kind of vessel, such as a blood bag, or slides having structures for defining liquid spots thereon.

The sample carrier can be embodied for holding a liquid sample with the volume of less than 1 µl to some deciliter.

As the sample carrier or the sample carriers are extending substantially parallel to the rotational axis, nearly the same centrifugal force is exerted to all the sample material. This applies for both a plurality of small tubes which are arranged substantially parallel to the rotation axis as well as a large sample vessel such as a blood bag which comprises its main extension in the direction parallel to the rotation axis.

The sample carrier receptacle can be also embodied for holding several sample carriers which are additionally extending substantially lateral to the rotation axis. In such a case it is appropriate that the sample carrier receptacle is arranged in a distance to the rotation axis which is substantially larger than the distance of a lateral extension of the sample carriers. The distance between the rotation axis and the sample carriers should be at least as large as the lateral extension and preferably at least two times or three times as large as the lateral extension of the sample carriers in the sample carrier receptacle. With such an arrangement, it is also achieved that nearly the same centrifugal force is exerted on all the sample material even if some sample carriers are arranged in a lateral extension with respect to the rotation axis.

A sample carrier centrifuge according to the present invention for rotating greater amounts of liquids can be embodied with a counterweight. The position of the counterweight can be automatically adjusted.

The liquid sample is preferably covered with a layer of oil. Such a layer of oil can be automatically added to the sample by a pippeting means. Such a layer of oil can reliably prevent the liquid sample from coming into contact with the air. In combination with using a centrifuge such a layer of oil can be provided on the bottom of a tube. By centrifugation of a layer of oil and a liquid probe above the oil layer the liquid probe is immersing through the oil layer so that the liquid probe is completely covered by the oil layer. Thus it is possible to firstly fill in an oil layer and afterwards the liquid sample which has to be covered by the oil layer. Thus tubes can be used being initially filled with an oil layer, wherein liquid samples can be immersed through the oil layers. This makes the covering of liquid samples easy to automate, as no lids have to be handled.

A further advantage of the centrifuge according to the present invention is that it needs less space of the platform in comparison to a centrifuge having a vertical rotating axis being perpendicular to the platform. Centrifuges with a vertical rotating axis have usually a rotor for taking up several samples which can only be jointly centrifuged. It is also necessary that all sample receptacles of an ordinary centrifuge are filled with a probe to have the rotor of the centrifuge in balance.

The horizontal axis according to the present invention allows the arrangement of several centrifuges on a platform, wherein each centrifuge can be separately controlled. So it is possible to centrifuge several samples individually from each other and they have not to be combined in a common batch (random access processing). The horizontal axis is rotatably fixed with both ends. So a larger degree of unbalance can be handled in comparison to a centrifuge with a horizontal rotating axis which is only fixed with one end. The centrifuges according to the present invention can thus be embodied with one single sample carrier receptacle. As the receptacle has to be able to carry samples with different weights the rotating parts of the centrifuge cannot always be perfectly balanced, because all samples in the single receptacle are placed on the same side of the rotating axis. Even if the sequentially centrifuged weights of the different samples are varying this does not compromise the operation of the centrifuge.

Other advantages that arise from the rotation axis being oriented parallel to the platform of the sample carrier centrifuge will become more apparent below in the advantageous modifications of the present invention, many of which are made possible simply by means of the relative arrangement of the platform and rotation axis as described in the main claim.

The relative arrangement of the platform and rotation axis of the sample carrier centrifuge according to the invention makes it possible for a sample carrier to be inserted into the holding section and accommodated in the sample carrier receptacle until the beginning of the centrifuging process, with its sample channel longitudinal axis extending in the direction of action of the force of gravity. To this end, it is advantageous if the sample carrier centrifuge has a rotation position sensor that detects a predetermined rotation position of the sample carrier receptacle, for example a rotation position in which a sample channel longitudinal axis of a sample channel accommodated in the holding section of the sample carrier receptacle is oriented extending in the direction of action of the force of gravity, so that the force of gravity acts in the same direction in which the centrifugal force generated by the centrifuging action is intended to act on the sample carrier. In this case, until the beginning of the centrifuging process, the force of gravity—not quantitatively, but qualitatively—has the same effect on the test-ready sample carrier as the subsequent centrifugal force.

The sensor can cooperate in an intrinsically known way with a marking formation on the sample carrier receptacle or on a component that is attached to it in a non-rotating way and can detect the presence or absence of the marking formation in the sensor measuring range. Likewise, the rotation position of the sample carrier receptacle can cooperate by means of a circumferential barcode that is mounted on the sample carrier receptacle, on a drive shaft of the latter, or on a component that is connected to it in a non-rotatable way or by means of other coding elements that are sensitive to the circumference position, which makes it possible to determine not only a predetermined rotation position, but any arbitrary rotation position of the sample carrier receptacle.

A sample carrier centrifuge that does not take up much space radially relative to the rotation axis can be achieved by the fact that the rotation axis passes through the sample carrier receptacle. Then the radial distance of the sample carrier receptacle from the rotation axis is small. This does mean that at the same speed of the sample carrier receptacle, a less powerful centrifugal force acts on the sample carrier receptacle with the rotation axis passing through it than acts on a sample carrier receptacle that is situated at a distance by means of a bar spaced apart from the rotation axis. However, as compared to a sample carrier receptacle that protrudes out from the rotation axis, a sample carrier receptacle that has the rotation axis passing through it reduces the mass moment of inertia, which is inherent in the mass that rotates around the rotation axis and which exerts a resistance to a rotational acceleration, so that with the same motor output, higher rotation speeds can in turn be achieved than in sample carrier centrifuges with higher mass moments of inertia. As a result, in sample carrier centrifuges that are otherwise the same in terms of drive, the reduction in centrifugal force to be initially feared due to the short distance of the sample carrier receptacle from the rotation axis can be at least partially compensated for once again.

The rotation axis preferably passes through the sample carrier receptacle eccentrically so that whereas an unloaded sample carrier receptacle, i.e. a sample carrier receptacle in which no sample channel has been placed, would in fact possibly have an imbalance when rotated around the rotation axis, a sample carrier receptacle that is loaded with a predetermined sample carrier has essentially no imbalance so that with the sample carrier centrifuge according to the present invention, it is possible to centrifuge a small number of sample channels, in particular a small number of sample carriers. This serves to further shorten the time interval that elapses between the test-ready installation of the sample carrier by introduction of a test substance into the reference substance that is usually provided in the sample channels and a test result obtained after a centrifuging process is completed.

In order to permit a secure holding of a sample carrier in the sample carrier receptacle, it is advantageous if the holding section holds the sample carrier in a form-locked fashion with regard to the expected direction of action of the centrifugal force, thus essentially preventing the sample carrier from breaking loose when the centrifugal force is exerted. This can be implemented through simple design means by embodying and arranging the sample carrier receptacle so that the main dimension direction of the holding section extends parallel to the rotation axis, both when the sample carrier receptacle is rotating and when it is not. With a holding section embodied in this way, it is possible in particular for the "gel cards," which are mentioned at the beginning and are preferably intended as the sample carrier receptacle, to be held in the holding section in the desired position relative to the rotation axis of the sample carrier centrifuge. Immediately after being inserted into the holding section, the sample carrier is thus correctly oriented for the subsequent centrifuging and does not need to be re-oriented, as is the case in some sample carrier centrifuges according to the prior art in which the sample carrier receptacles, driven by the centrifugal force, pivot into an end position in which the sample carrier longitudinal axes finally extend orthogonally to the rotation axis for the first time. Consequently, from the time at which the sample carrier is inserted into the holding section to the time at which it is removed from the holding section, the sample carrier is accommodated in the sample carrier receptacle in such a way that a sample channel longitudinal axis of the sample channel provided in the sample carrier is always oriented essentially orthogonal to the rotation axis and is therefore oriented in the expected direction of action of the centrifugal force.

For an optimum action of the centrifugal force as the driving force for a penetration of the test substance into the reference substance of a sample channel of the sample carrier, it is advantageous if the sample channel longitudinal axis is spaced apart from the rotation axis by a radial distance that is not greater than the greatest radial dimension of the sample channel in a radial direction that is essentially orthogonal to both the sample channel longitudinal axis and the rotation axis.

As a result, the sample channel longitudinal axis can always be assumed to be the most central possible longitudinal axis through the respective sample channel. Since the inner boundary surface of a sample channel is usually embodied as rotationally symmetrical, however, determining the sample channel longitudinal axis is not problematic because the sample channel longitudinal axis coincides with the axis of symmetry. Therefore the greatest distance between the sample channel longitudinal axis and the inner wall of the sample channel should be used as the greatest radial dimension of the sample channel.

Furthermore, the radial dimension of the sample carrier centrifuge and therefore the amount of space that the sample carrier centrifuge takes up can be kept advantageously small if the axial distance of the sample carrier from the rotation axis in the direction of the sample channel longitudinal axis is less than the dimension of the sample carrier in this axial direction, in particular is less than the axial length of the sample channel on the sample carrier, preferably is less than half the length of the sample channel, and particularly preferably is less than one fifth the length of the sample channel. As a rule, the sample channel is shorter than the sample carrier, which usually provides space for labels and the like on the sample carrier axially below the sample channel or sample channels in relation to the sample channel longitudinal axis.

In a particularly advantageous way from a design standpoint, the holding section can be composed of only two subassemblies, i.e. of only two side walls essentially parallel to the rotation axis between which the rotation axis passes and between which the holding section is defined. Although each wall is preferably embodied of one piece in order to have an advantageously low number of parts, this should not exclude the option of one or both walls being composed of several parts.

A section of each side wall, which is referred to below as the "partition wall section," can be embodied on each side wall in order to delimit a receiving opening into which a sample carrier can be inserted so that it can be accommodated in the sample carrier receptacle. This delimitation is essentially a delimitation whose direction is orthogonal to a parallel rotation axis so that the receiving opening, in particular for accommodating the preferred sample carriers in the form of "gel cards," is embodied in the form of a slot-shaped opening with a main dimension direction parallel to the rotation axis.

In order to achieve a long service life with operation at the highest possible speeds and therefore with the most powerful possible centrifugal forces on the sample carrier, it is advantageous if the sample carrier receptacle is balanced in relation to a predetermined sample carrier so that when rotating around the rotation axis, the unloaded sample carrier receptacle has a greater imbalance than the sample carrier receptacle loaded with the predetermined sample carrier. The greater imbalance of the sample carrier in the unloaded state is reduced, preferably to zero, by the insertion of a predetermined sample carrier.

The ability of the sample carrier receptacle to be balanced while at the same time having small dimensions orthogonal to the rotation axis of the sample carrier centrifuge is significantly facilitated by the above-mentioned advantageous fact that the rotation axis passes eccentrically through the sample carrier receptacle. For balancing purposes, the sample carrier receptacle can have a balancing section, for example a set of weights, which is provided with a correctly calculated weight at a correctly calculated location of the sample carrier receptacle. The balancing of a rotating part is sufficiently known in expert circles to render a detailed discussion of it here unnecessary. The weights required in the balancing section can be kept advantageously smaller the farther the balancing section is located from the rotation axis. For this reason, it is preferable for the partition wall section of the undesignated side walls accommodating a sample carrier to be positioned closer to the rotation axis than the balancing section.

Although the option of providing the balancing section as separate from the partition wall section or entirely separate from the side walls should not be excluded, it is nevertheless preferable, for the sake of minimizing the number of parts, if the balancing section is provided on a side wall and preferably, is integrally joined to it.

In order to avoid providing a balancing section close to a loading trajectory along which a sample carrier is inserted into the sample carrier receptacle and unloaded from it again and thus potentially hindering a loading and unloading of the sample carrier receptacle, it is advantageous if the sample carrier centrifuge has a plurality of balancing sections. These can therefore be provided on the sample carrier receptacle so as to permit an unhindered loading and unloading of sample carriers into and out of the sample carrier receptacle.

Preferably, the sample carrier centrifuge has as many balancing sections as it does side walls. Preferably, each side wall is provided with a respective balancing section. Then the balancing section can be provided either on an associated side wall or, in order to minimize the number of parts, can be integrally joined to an associated side wall. In this case, the side wall itself can constitute the balancing section.

If the distance between the side walls in the vicinity of the balancing sections increases as the distance from the holding section increases and as the distance from the rotation axis increases, then sufficient clearance in the holding section can be provided for the loading of the sample carrier receptacle even by automated loading mechanisms and their grasping devices for grasping sample carriers. It is also conceivable to embody the balancing sections in the shape of funnels that feed toward the holding section and therefore to use them as insertion-facilitating elements for sample carriers or sample carrier grasping devices of loading machines. The partition wall section and the balancing section of a side wall thus preferably enclose an angle. This can be an obtuse angle, i.e. an angle greater than 90°, so that the balancing section of a side wall can be used directly to facilitate insertion of a sample carrier into the holding section defined by the partition wall section. A rounding of the transition from the balancing section to the partition wall section thus permits the balancing section to smoothly guide a sample carrier resting against it into the partition wall section and thus into the holding section.

Preferably, however, the partition wall section and the balancing section of a side wall enclose an acute angle since this makes it possible to produce a sample carrier receptacle that is less spread out in the radial direction and has a lower mass moment of inertia with the same mass.

Slight imbalances even at higher speeds of the sample carrier centrifuge can still be tolerated if the sample carrier receptacle is mounted to a centrifuge housing at two bearing points spaced apart from each other in the direction of the rotation axis and is able to rotate around the rotation axis relative to this housing, with the holding section then provided between the bearing points.

According to a less preferred embodiment of the present invention, a sample carrier receptacle that has a floating support on one side is in fact basically also conceivable, particularly when the loading and unloading of it are to occur with a loading trajectory parallel to the rotation axis. However, the above-described loading state of the sample carrier receptacle is preferable due to the significantly improved true running.

In order to be able to place the rotary drive unit of the sample carrier receptacle as close as possible to the sample carrier receptacle, a bearing point of the sample carrier receptacle can be provided between the holding section and a drive section of the sample carrier receptacle in order to introduce the rotation drive force of a rotation drive unit. It is thus possible for the drive shaft to be short and especially for it to be supported by means of a bearing that helps to significantly reduce a tendency of the drive shaft to oscillate at high speeds.

Preferably, the rotation axis of the sample carrier receptacle coincides with the rotation axis of an output shaft of a rotary drive unit, in particular an electric rotary drive unit. In this case, the drive unit can drive the sample carrier receptacle directly, i.e. without an interposed speed-increasing or speed-decreasing transmission. This not only further reduces the number of parts required, it also produces a sample carrier centrifuge that takes up an advantageously small amount of space so that it can also be used in laboratories in which only a small amount of space for setting up laboratory devices is (still) available.

In order to achieve a sample carrier receptacle imbalance that is advantageously as slight as possible, this sample carrier receptacle is embodied as mirror-symmetrical relative to a symmetry plane containing the rotation axis.

Since with the agglutination reaction tests mentioned at the beginning, there are frequently a plurality of conceivable possibilities for combining bodies and antibodies, a sample carrier advantageously has a plurality of sample channels so that one sample carrier can be used to test a plurality of or even all of the possible permutations of bodies and antibodies. The plurality of sample channels of a sample carrier are then preferably parallel to one another and preferably even lie in a common sample carrier plane, resulting in a sample carrier, which, except for the protuberance of the sample channels, is flat and card-like, as in the kind known as a "gel card" or "bead cassette." In the context of the present application, when associating a sample carrier with the term "gel card," it is unimportant whether a gel is actually is contained in the sample channels or whether they contain a different reference substance. The term "gel card" refers solely to the design of a preferred sample carrier.

A classic example of the agglutination reaction test is a test for determining a blood group. In a simplified description, blood contains red blood corpuscles, so-called "erythrocytes" whose outer membrane has an antigen structure that corresponds to the respective blood group. The erythrocytes of blood group A have the A antigen structure, erythrocytes of blood group B have the B antigen structure, the erythrocytes of blood group AB have both the A and B antigen structures, and erythrocytes of the blood group O have no antigen structure at all.

In addition, blood has antibodies that are designed to couple to an antigen structure that is different from the antigen structure of the erythrocytes belonging to said blood group. By coupling to the respective antigen structures, the antibodies produce an agglutination reaction, which is referred to for the sake of simplicity as a clumping reaction. Blood of the blood group A has the antibody against antigen structure B. By contrast, in blood group B, the antibodies are against antigen structure A. Since the blood group AB has erythrocytes with both antigen structures, it cannot contain any antibodies while the blood group O typically has antibodies against both the A antigen structure and the B antigen structure.

If antibodies with a known antigen structure orientation are added to a blood sample of an unknown blood group, then its blood group can be determined by means of agglutination. When centrifuging, the rate of agglutination can be determined by the different migration depth of the respective blood sample into the reference substance since with a uniform driving force, samples of a test substance with different agglutination rates migrate to different depths into a test substance.

If the sample carrier plane of a sample carrier that is inserted into the sample carrier receptacle, i.e. generally the plane of its main dimension, contains the rotation axis or is parallel to the rotation axis and spaced apart from it by a distance that is not greater than the greatest radial dimension of one sample channel out of the plurality of sample channels of the sample carrier in a radial direction that is essentially orthogonal both to the sample channel longitudinal axis of the sample channel and to the rotation axis, then it is possible to ensure that the centrifugal force that occurs during the centrifuging process essentially coincides with the sample channel longitudinal axes of the respective sample channels or deviates from them by only an insignificant amount that is easily tolerated. This ensures the functionality of the sample carrier during the centrifuging process. The term "sample carrier plane" here is a theoretical plane extending beyond the edges of the sample carrier.

The sample carrier receptacle can be embodied to accommodate a plurality of sample carriers, which are then preferably placed one behind the other in a sample carrier receptacle that is axially long relative to the rotation axis so that the sample carrier longitudinal axes of all of the sample carriers that are accommodated in a sample carrier receptacle lie in a common plane. In order to ensure the quickest possible processing of a sample carrier, however, the sample carrier receptacle is preferably embodied to accommodate exactly one sample carrier. On the one hand, this produces a sample carrier receptacle that is short in the axial direction relative to the rotation axis and that does not tend to oscillate or only has a significantly less pronounced tendency to oscillate during rotation operation; on the other hand, this ensures that a test-ready sample carrier can be centrifuged immediately since no further sample carriers can be loaded into the sample carrier receptacle.

First, in order to protect the sample carrier during the centrifuging process and second, in order to protect laboratory personnel and laboratory devices in the immediate vicinity of the sample carrier centrifuge in question here, the sample carrier centrifuge can be provided with a centrifuge housing equipped with an access opening that can be closed and opened by means of a cover movably mounted to the centrifuge housing. Preferably, a separate drive motor for opening and closing the access opening by means of the cover is provided, which, particularly with the above-mentioned direct coupling of the sample carrier receptacle to the output shaft of a rotary drive unit can be provided next to the rotary drive motor of the sample carrier receptacle without taking up additional space that would increase the size of the centrifuge housing. For example, the drive motor for the cover can also be an electric drive motor whose output shaft can be oriented parallel to the output shaft of the rotary drive unit for the sample carrier receptacle.

In this case, the centrifuge housing takes up the least amount of space possible if an inner surface of the centrifuge housing oriented toward the sample carrier receptacle and/or an inner surface of the cover oriented toward the sample carrier receptacle—in at least parts of their circumference and preferably along their entire span in the circumference direction around the rotation axis—is/are embodied in the form of a cylinder or partial cylinder whose cylinder axis is the rotation axis.

In order to evaluate sample carriers as quickly as possible even during centrifuging, a sample carrier centrifuge can have a camera or another optical recording device that is oriented with its optical axis so that it records the sample carrier accommodated in the holding section.

Consequently, immediately after the sample carrier receptacle stops in a predetermined position, for example with a sample carrier plane orthogonal to the optical axis of the camera, which position can be detected by the above-mentioned sensor and can intentionally be approached by means of a regulating device that cooperates with the sensor, a recording of the sample carrier can be made, which is transmitted via corresponding data lines to an image processing evaluation unit for evaluating the status of the sample carrier after the centrifuging process.

If the sample carrier centrifuge is additionally equipped with a flash unit or stroboscope, then the above-mentioned camera can be used to carry out an evaluation of the sample carrier "online," even during the centrifuging process.

To accomplish this, the flash unit or the stroboscope can be coupled to a rotation position-detecting sensor and/or to the rotary drive unit of the sample carrier receptacle via a data transmission coupling so that it triggers a flash when the rotating sample carrier is in a predetermined rotation position that is particularly advantageous for the optical axis of the camera, for example with the at least one sample channel longitudinal axis oriented orthogonal to the optical axis.

In order to process a plurality of sample carrier receptacles, which are awaiting centrifuging at different time intervals that are shorter than the duration of centrifuging required for a single test, it is possible for the sample carrier centrifuge to be equipped with a plurality of sample carrier receptacles, preferably with parallel rotation axes and particularly preferably with one centrifuge housing per sample carrier receptacle. Preferably, the sample carrier receptacles can be individually driven. This produces a sample carrier centrifuge that can be composed in modular fashion of the above-described sample carrier centrifuges, which are then referred to as sample carrier centrifuge modules or sample carrier sub-centrifuges. Each of these separate sample carrier centrifuge modules, however, taken individually, is preferably embodied and functions in accordance with the above description.

Although the sample carrier centrifuge modules can in fact also be basically arranged with coinciding, i.e. coaxial, rotation axes, the parallel arrangement of rotation axes is preferable because otherwise, sample carrier rotary drive units are situated between successive sample carrier receptacles, as a result of which the modularly constructed sample carrier centrifuge can be complex in appearance. In the preferred case of parallel rotation axes, the sample carrier receptacles can be placed next to one another in a very limited space, thus facilitating their automated loading and unloading so that the sample carriers to be centrifuged no longer have to be moved by operating personnel but can instead be moved by automated devices, thus advantageously reducing the risk of contamination of the samples in the sample carrier.

For the sake of facilitating an automated handling of sample carriers and a particularly desired automated loading and unloading of the modularly constructed sample carrier centrifuge, it is possible for the rotation axes of the plurality of sample carrier receptacles to be essentially situated in a common rotation axis plane. Preferably, the platform of the sample carrier centrifuge is then parallel to the rotation axis plane.

It is thus conceivable to produce a centrifuge arrangement in which the loading and unloading of one or more sample carrier receptacles can be carried out by a loading machine and/or the equipping of a sample carrier with the sample can be carried out in automated fashion on the sample carrier that is already accommodated in the sample carrier receptacle. A pipetting device can be provided for equipping (test-ready equipping) the sample carrier with a sample.

These advantages of the automation can therefore be achieved with a centrifuge apparatus including a sample carrier centrifuge with an essentially horizontally arranged rotation axis, as described above, and also including a pipetting device for automatically dispensing a fluid into a sample channel of a sample carrier held in the at least one sample carrier receptacle; the pipetting device has a pipetting channel extending essentially in the vertical direction, which is movable preferably along a vertical movement axis and additionally or alternatively to the pipetting device, the centrifuge arrangement includes a loading machine for automated loading and unloading of the at least one sample carrier receptacle and the loading machine is arranged with an essentially vertical loading trajectory.

This specific desired degree of automation is made possible by the ability to arrange the rotation axis or axes horizontally, which once again is a result of the platform of the sample carrier centrifuge being oriented parallel to the rotation axis. The pipetting channel extending in the vertical direction is advantageous since the dispensing of a test substance into the sample carrier is assisted by the force of gravity and can therefore occur with the least amount of dripping possible, i.e. without the occurrence of contamination. The loading trajectory of the loading machines, at least in an end section close to the holding section, preferably likewise extends vertically since in this case, the sample carrier receptacle can be supported in a particularly stable fashion in the above-described way by means of two pivot bearings between which the holding section is accommodated. Consequently, the space above the at least one horizontally arranged rotation axis of the sample carrier centrifuge can be used for handling sample carriers and/or for dispensing the test substance into the sample carriers. This is further encouraged by the above-described advantageous modification according to which the sample carrier receptacle can be accommodated in a predetermined preferred position. In the present case, this preferred position would be the one in which the at least one sample channel longitudinal axis of the at least one sample channel of a sample carrier is arranged essentially vertically; then a longitudinal test substance-introducing end of the at least one sample channel with which the test substance is properly introduced into the sample channel is positioned higher than its opposite axial longitudinal end in relation to the sample channel longitudinal axis.

In order to prevent collisions between the pipetting device and the loading machine or in order to minimize the risk of this happening, the pipetting device and/or the loading machine is/are preferably movable in the horizontal direction.

The centrifuge according to the present invention can be easily implemented in an automatic liquid handling system. Such liquid handling system can comprise a pipetting robot, one or more thermocyclers, a storage for reagents and/or other liquid handling devices.

A further aspect of the present invention is the use of an oil layer for sealing a liquid sample in combination with a centrifuge. As described above the liquid sample can immerse the oil layer by centrifuging the vessel containing the oil layer and the liquid sample. It is also possible to expel any air bubble in the liquid sample covered by the oil layer just by centrifuging the vessel. It is also possible to add at separate steps separate reagents and to immerse the reagents stepwise through the oil layer.

The aspect of the present invention of using an oil layer for sealing a liquid sample is independent of the design of the centrifuge. However, the use of an oil layer simplifies the automation of handling liquid samples and can thus be advantageously combined with a centrifuge having a rotation axis parallel to the platform.

The present invention will be explained in greater detail below in conjunction with the accompanying drawings. In the drawings:

FIGS. 1 through 3 show an embodiment of a sample carrier centrifuge according to the invention, which is labeled as a whole with the reference numeral 10.

The sample carrier centrifuge can have a possibly multipart centrifuge housing 12, which can accommodate the drive unit and centrifuge components so that they are protected from external influences.

The centrifuge housing 12 can be composed of individual housing modules, each of which houses a respective sample carrier receptacle 14. In the examples shown in FIGS. 1 through 3, however, this is not the case. The drawings all show sample carrier receptacles accommodated in a shared centrifuge housing 12.

Figure 1:
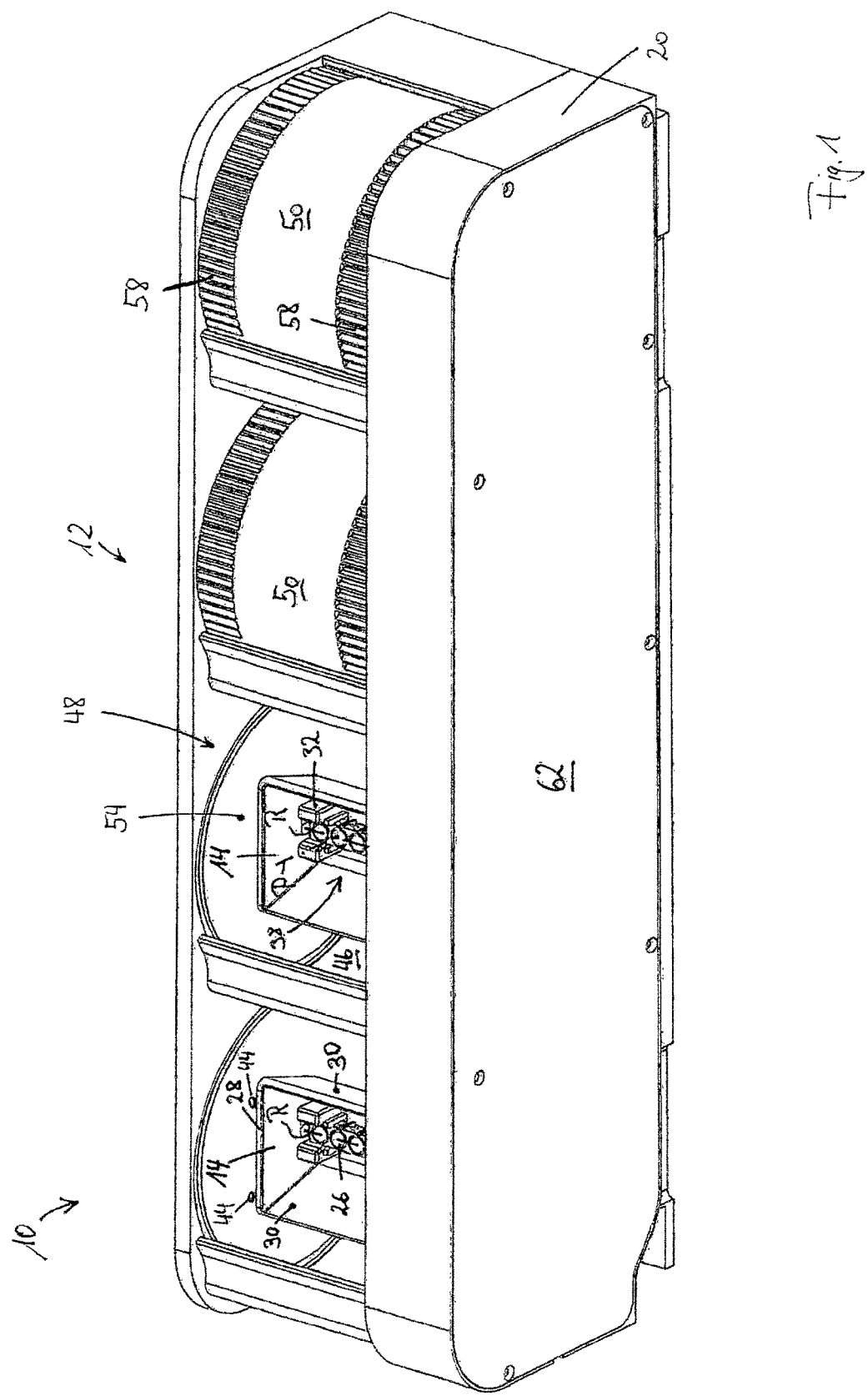
FIG. 1 is a perspective top view of an embodiment of a sample carrier centrifuge according to the invention.
Figure 2:
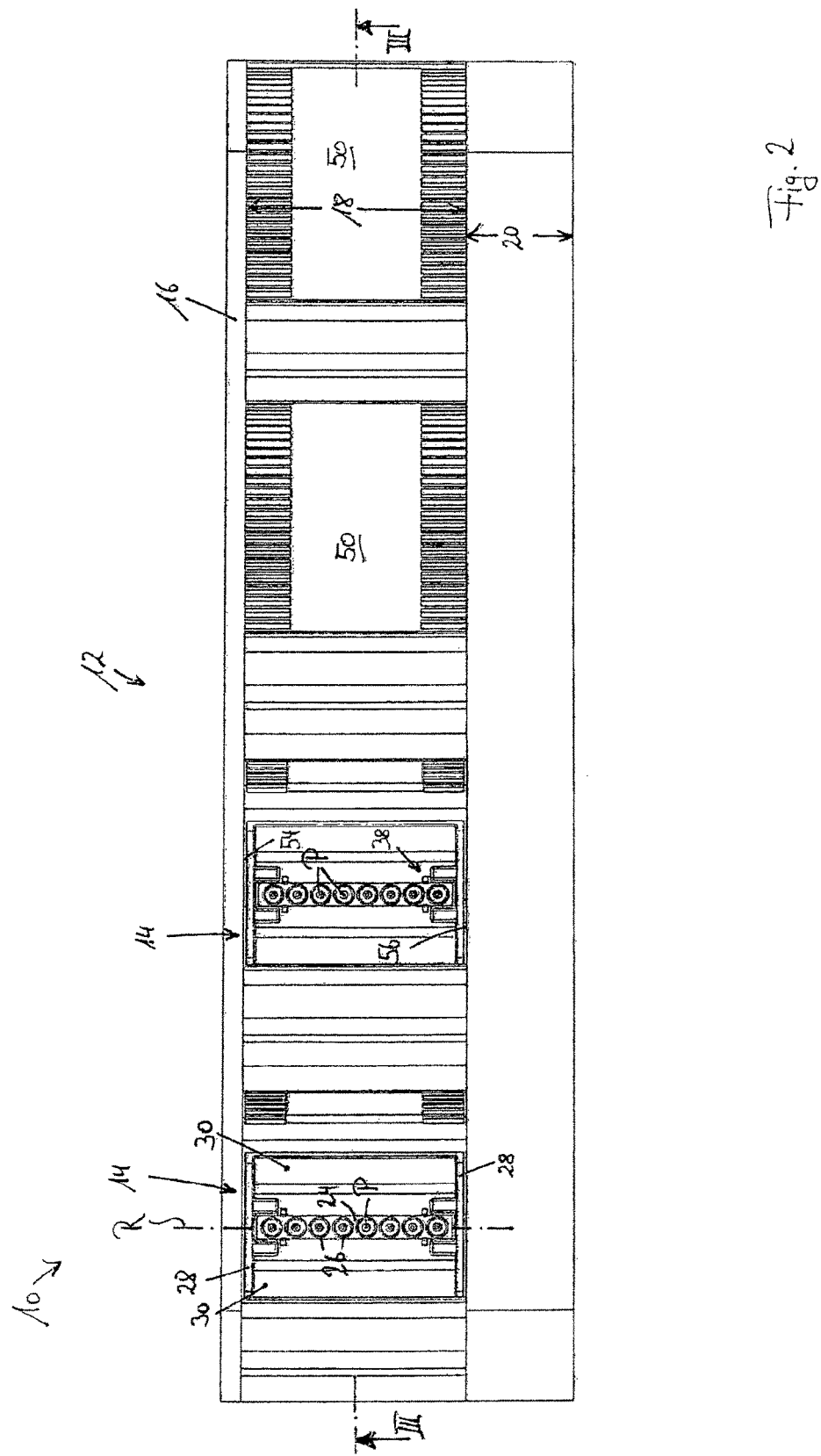
FIG. 2 is a top view of the sample carrier centrifuge from FIG. 1.
Figure 3:
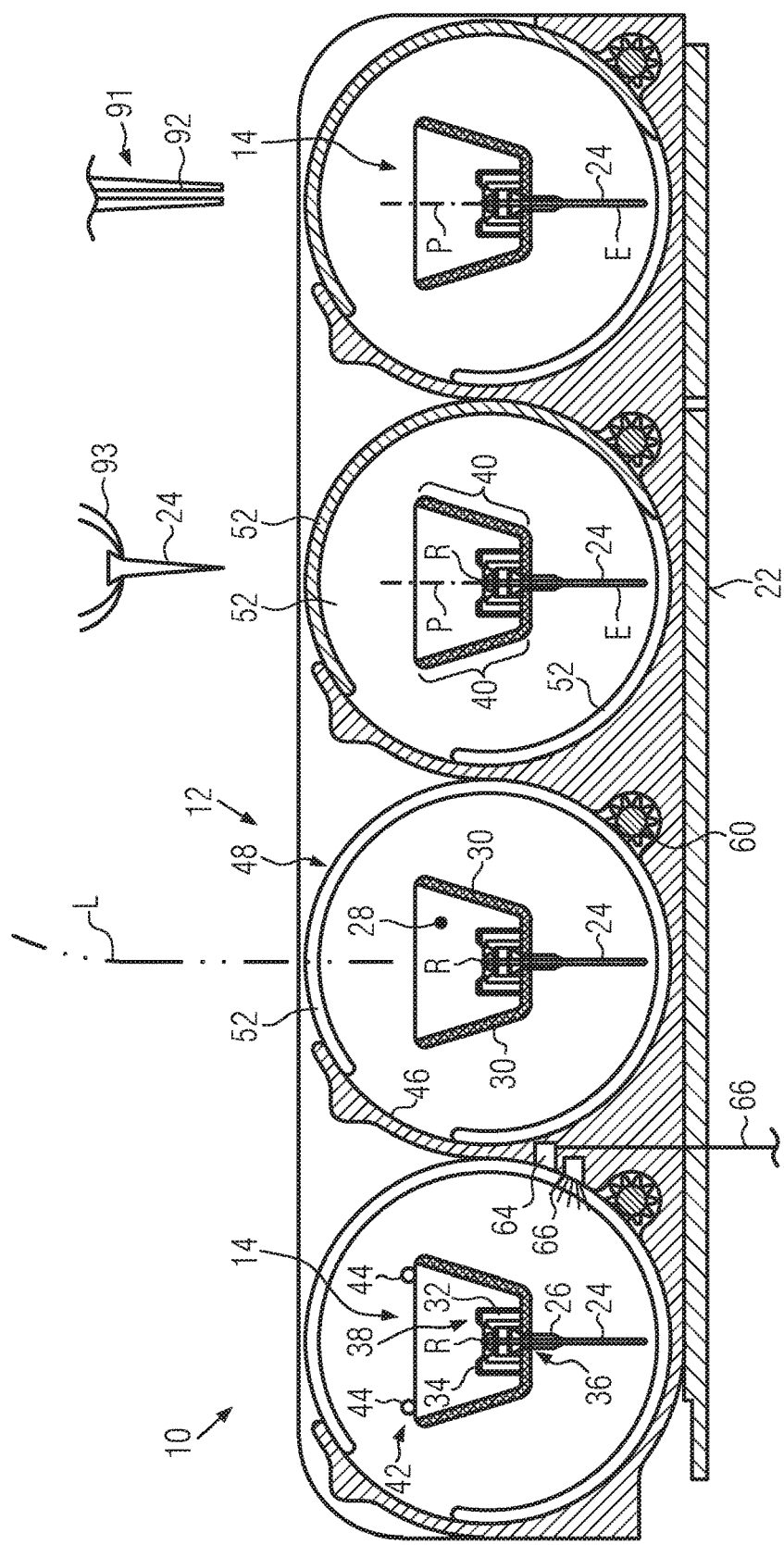
FIG. 3 is a cross-section through the sample carrier centrifuge in FIGS. 1 and 2 along the intersecting plane III-III from FIG. 2.

The embodiment of the sample carrier centrifuge 10 shown in the present example in FIGS. 1 and 2 has four preferably identical sample carrier receptacles 14, as particularly shown in FIG. 3.

The sample carrier receptacles 14 can each be rotated around a rotation axis R and each sample carrier receptacle 14 is preferably associated with its own rotation axis R. Each rotation axis R preferably passes through its associated sample carrier receptacle 14 in an eccentric fashion, as particularly shown in FIG. 3. The rotation axes R of all of the sample carrier receptacles 14 lie in a common plane, which in the present exemplary embodiment is parallel to the plane of the drawing in FIG. 2 and orthogonal to the plane of the drawing in FIG. 3.

The centrifuge housing 12 preferably has a bearing section 16, a sample carrier receptacle section 18, and a drive section 20, which are preferably arranged one after the other in the direction of the rotation axes R, as primarily shown in FIG. 2.

The bearing section 16 preferably contains first bearing means for rotary support of the sample carrier receptacles 14 around the rotation axis R. The sample carrier receptacle section 18 preferably contains the sample carrier receptacles 14 themselves so that they are able to rotate around the rotation axis R; the drive section 20 preferably contains additional bearing means for supporting the sample carrier receptacle 14 in rotary fashion around the rotation axis R and also contains the rotary drive unit of the sample carrier receptacle 14.

In order to achieve a stable and rigid rotary support of the sample carrier receptacles 14, preferably the second bearing means—relative to the associated rotation axis R—is axially situated between the sample carrier receptacle 14 and the drive unit that drives this sample carrier receptacle 14.

As is particularly visible in FIG. 3, the sample carrier centrifuge 10 and in particular, its centrifuge housing 12, has a platform 22 that is essentially flat and parallel to at least one, preferably all, of the rotation axes R of the exemplary embodiment shown. Preferably, the platform 22 is parallel to a plane containing the rotation axes R. This enables the compact design of the sample carrier centrifuge 10 shown in FIGS. 1 through 3, with an advantageous, automated loading with sample carriers 24 from above and/or with possibly automated dispensing of a test substance into a sample carrier 24 already situated in a sample carrier receptacle 14.

The preferred sample carriers 24 shown in the present example are embodied in the form of so-called "gel cards" that in the present example, each have eight respective sample channels 26 that are preferably embodied as essentially identical.

The sample channels 26 in the present example are preferably embodied with a rotationally symmetrical inner wall in relation to a sample channel longitudinal axis P that passes essentially centrally through the sample channels 26 along their longitudinal direction. Preferably, as in the "gel cards" 24 shown in FIGS. 1 through 3, the sample channel longitudinal axes P of the sample channels 26 of a sample carrier 24 lie in a common plane, namely the plane E of the sample carrier 24 extending orthogonal to the plane of the drawing in FIG. 3.

The sample carrier receptacles 14 can be advantageously embodied as trough-like. Basically, however, any other design is also conceivable.

In the example shown in FIGS. 1 through 3, the identical sample carrier receptacles 14 have end walls 28 in their longitudinal end regions, between which side walls 30 can extend on either side of the rotation axis R. The end walls 28 are preferably positioned orthogonally relative to the rotation axis R in order to be able to embody the sample carrier receptacles 14 to be as short and functional as possible relative to the rotation axis R.

At the longitudinal ends of the sample carrier receptacles, partition wall sections 32 can be provided, which can have latching elements 34, possibly in the form of latches extending toward a receiving opening 36 of the sample carrier receptacle 14, that hold the sample carriers 24 securely in the sample carrier receptacle 14 and reduce the potential of an undesirable detachment of dropping from the sample carrier receptacles 14. The partition wall sections 32, which in the example shown, are only provided in the longitudinal end sections of the sample carrier receptacle 14 on both sides of the receiving opening 36, can also extend farther into the sample carrier receptacle 14 along the rotation axis R starting from one longitudinal end, can be provided in a middle section instead of at the longitudinal ends, or can extend over the entire length of the sample carrier receptacle 14.

For the sake of better comprehension, it should be noted that in the FIGS. 1 through 3 used here, the sample carrier receptacles 14 and each individual centrifuge module are each embodied as essentially identical to all of the other similar components so that reference numerals that are in fact applicable to all similar components are provided only to components selected by way of example in order not to overload the drawings with reference numerals and in order to give a clear depiction of the sample carrier centrifuge 10.

Instead of the protruding latches, it is also possible to provide other latching means 34, for example projections, ball catches, and the like that move resiliently forward and back in relation to the plane E of the sample carrier 24 situated in the sample carrier receptacle 14.

As shown particularly in FIGS. 2 and 3, the receiving opening 36 of the sample carrier receptacle is preferably situated on a radial line extending out from the rotation axis R so that the sample carrier longitudinal axes P of the sample carriers 24 inserted into the receiving opening 36 advantageously intersect the rotation axis R of the sample carrier centrifuge 10. This is not, however, an absolute requirement. The sample carrier longitudinal axes P can also pass by spaced slightly apart from the rotation axis R, for example by a distance that is not greater than the greatest radial dimension of a sample channel 26 starting from the sample channel longitudinal axis P. This specifically ensures that during the centrifuging process, a direction of action of a centrifugal force acting on the sample channels 26 is situated at least partially within the sample channel 26, which ensures an effective centrifuging process.

It is also clear from FIG. 3 that when sample carriers 24 are inserted into the receiving opening 36, the longitudinal end of the sample channels 26 closer to the rotation axis is situated on the rotation axis. As a result, it is possible to achieve a centrifuge housing 12 that is radially very short in relation to the rotation axis R and takes up a small amount of space.

The distance of the longitudinal end of the sample channels 26 closer to the rotation axis from the rotation axis R of the sample carrier centrifuge 10, however, does not have to be zero. It can be less than the dimension of the sample carrier 24 in the direction of the sample carrier longitudinal axis P and can in particular be shorter than the length of the sample channels 26.

In the example shown, the loading and unloading of the sample carrier receptacle 14, in particular of the holding section 38 preferably composed of the receiving opening 36 and the partition wall sections 32, can take place preferably from above, i.e. by means of an essentially vertically oriented loading trajectory L that advantageously lies in the plane E of the sample carriers 24 in the loaded state of the sample carrier receptacle 14.

In order to facilitate the loading and unloading, for example by means of grasping tools of a loading machine, the distance between opposing side walls 30 preferably increases with the distance from the rotation axis R so that side walls 30 belonging to one and the same sample carrier receptacle 14 can form a sort of funnel.

As is clear from FIG. 3, the rotation axis R passes eccentrically through the sample carrier receptacle 14 that advantageously extends essentially parallel and along it because when looking at the sample carrier receptacle 14 in a cross-section with an intersecting plane extending orthogonal to the rotation axis, the rotation axis R does not lie in a center of area of the envelope of the cross-sectional image of the sample carrier receptacle 14. In FIG. 3, in the exemplary embodiment shown here, this envelope has a trapezoidal shape with rounded corners and the longer of the two parallel trapezoid bases in FIG. 3 is situated above the shorter of the two parallel trapezoid bases.

By means of this preferred eccentricity of the rotation axis R relative to the sample carrier receptacle 14, is possible to produce an advantageous balance situation in which the sample carrier receptacle 14 does in fact have an imbalance relative to a rotation around the rotation axis R in the unloaded state, but this imbalance can be reduced or even eliminated by loading it with a predetermined sample carrier 24. This purpose is also served by sections of the side walls 30, referred to as "balancing sections" 40 in the present application, which are preferably provided so that a sample carrier receptacle 14 with predetermined sample carriers 24 inserted into it can rotate around the rotation axis R essentially without any imbalance.

For the loading and unloading of the holding section 38 of a sample carrier receptacle 14, the sample carrier centrifuge 10 can be provided with a sensor unit 42, which detects the preferred loading and unloading position of the sample carrier receptacle 14 relative to the platform 22 shown in FIG. 3. This can be carried out, for example, by means of two sensors 44, for example proximity sensors or photodiodes, which are provided so that they only emit a coinciding signal when the sample carrier receptacle 14 is in the predetermined position. Alternatively, the sensors can also be provided on the drive shaft, which is not shown here, or on a component that rotates along with this shaft or can cooperate with this component.

In the same way that the loading and unloading of the embodiment of a sample carrier centrifuge 10 according to the invention in question here can occur along an essentially vertical loading trajectory L, a virgin sample carrier 24 with the reference substance provided therein can also be first inserted into a sample carrier receptacle 14 and can then be equipped with a test substance dispensed from above by a pipetting device 91. Consequently, the sample carrier 24 can be centrifuged immediately after being equipped with the test substance, thus also making it possible to carry out time-sensitive tests with the sample carrier centrifuge 10 in question here.

On the one hand in order to protect the sample carrier 24 during centrifuging and on the other hand in order to protect surrounding laboratory equipment and the involved laboratory personnel, the centrifuge housing 12 can have a partially cylindrical inner wall 46, which encompasses the sample carrier receptacle 14 and whose partial cylinder axis preferably coincides with the rotation axis R. An only partially cylindrical embodiment of the inner surface 46 is advantageous because this creates an access opening 48 through which a sample carrier 24 can be loaded, unloaded, and/or pipetted.

In order to close the access opening 48, a preferably likewise partially cylindrical cover 50 can be provided, which preferably likewise has the rotation axis R as the axis of the partial cylinder and can be guided in a groove 52 in the side walls 54 and 56 orthogonal to the rotation axis R in order to execute a circular motion around the rotation axis R.

Of the four modules shown in FIG. 3, the cover 50 has been omitted from both of the centrifuge modules on the left for the sake of better visibility.

The cover 50, preferably on its large circumference surface, can have at least one engagement formation 58, preferably a plurality of engagement formations 58, for example in the form of a denticulation, that a counterpart engagement formation 60, e.g. a gear, provided in the centrifuge housing 12 can drive with form-locked engagement to execute an opening and closing motion in order to enable an opening or closing of the access opening 48 in accordance with the wishes of an operator or in accordance with a predetermined sequence, for example depending on the approach of a loading machine 93 grasping device and/or of a pipetting channel 92. To this end, the motor section 20 of the centrifuge housing 12 can be provided with a separate cover drive unit, which can drive the counterpart engagement formations 60 in both possible movement directions.

On its side oriented away from the sample carrier receptacle section 18, the drive section 20 of the centrifuge housing 12 can be accessed by means of a removable back plate 62 for maintenance and repair.

With the sample carrier centrifuge 10 presented here, it is possible, while taking up the least amount of space possible, to centrifuge single sample carriers 24 as well as a plurality of sample carriers 24 in the shortest amount of time after they have been equipped with a testing substance.

In order to also be able to reduce the evaluation time, the centrifuge housing 12 can be provided with a camera 64, which in connection with a stroboscope 66, can, even during the centrifuging process, send an image of the sample carrier 24 to an evaluation unit, not shown, when the sample carrier receptacle 14 is in the position shown in FIG. 3, which is also an evaluation position. For this purpose, the stroboscope 66 can cooperate with the sensors 44 of a sensor arrangement 42 to trigger flash units.

Preferably, therefore, the loading and unloading position and the evaluation position of the sample carrier receptacle 14 are one and the same position so that both of these positions can be detected with a single sensor unit 42.

Figure 4A:
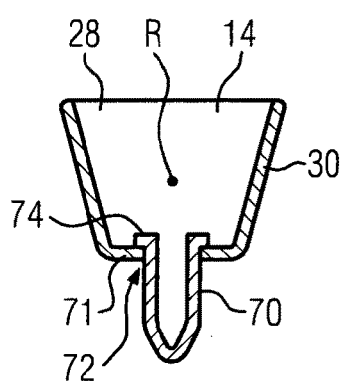
FIG. 4a-4e show sample carrier receptacles for holding tubes and microtiter plates in a cross-section view, a side view, top views and a perspective view.
Figure 4B:
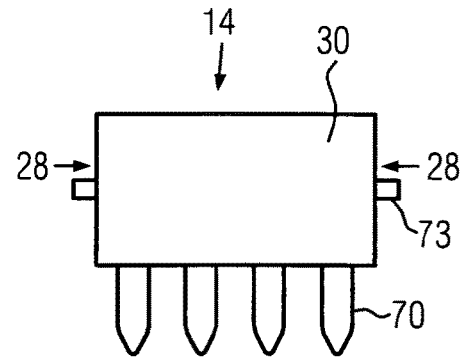
Figure 4C:
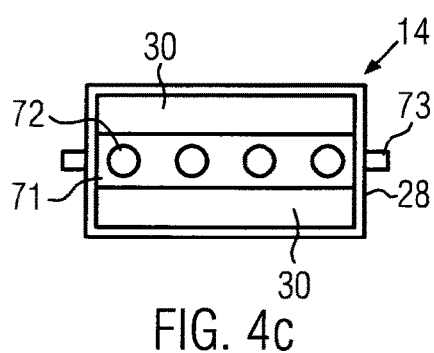

FIGS. 4a, 4b, and 4c show a sample carrier receptacle 14, which is embodied for holding a number of individual tubes 70. The receptacle 14 of FIGS. 4a and 4b replaces the corresponding receptacle in the centrifuge according to FIGS. 1 to 3. The receptacle 14 comprises end walls 28 and side walls 30 and a bottom wall 71. Several receiving openings 72 are provided in the bottom wall. One tube 70 can be placed in each receiving opening 72.

The tube 70 is provided at it's upper end with a circular flange 74, which secures the tube 70 in the bottom wall 71. The embodiment shown in FIGS. 4a and 4b has four receiving openings 72 arranged in-line. The receptacle 14 can be embodied with any other number of receiving openings 72. Although a different arrangement of the receiving openings 72 is basically possible. The receptacle 14 is rotated around the rotational axis R. Bearing pins 73 are provided at the outer surfaces of the end walls 28 in-line with the rotation axis R. One of these bearing pins 73 is engaged with a driving motor (not shown) for rotating the sample carrier receptacle 14 around the rotation axis R.

The weight of the receptacle 14 is significantly larger than the weight of the tubes 70 and their potential content. Furthermore, the mass centre of the receptacle is close to the rotational axis R. As the weight of the tubes 70 is rather small in comparison to the weight of the receptacle, the moment of inertia is slightly influenced and the mass centre is only shifted a little by the weight of the tubes, so that the centrifuge can be operated with a high rotational speed, even if it is loaded with no tube or with four tubes 73, which are all filled with a liquid sample.

The sample carrier receptacle 14 according to FIGS. 4a, 4b, 4c has the four receiving openings 72 arranged in-line. These receiving openings 72 are arranged parallel to the rotating axis R.

Figure 4D:
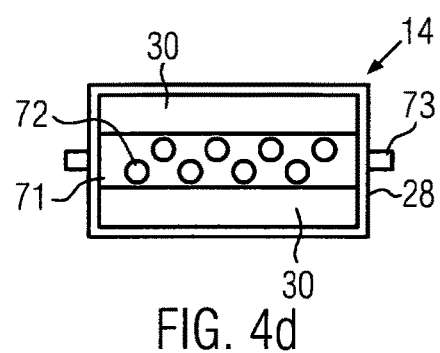

FIG. 4d shows a similar sample carrier receptacle 14, which differs from the one according to FIG. 4a-4c only in that the receiving openings 72 are not arranged exactly in-line but are arranged in zig-zag form so that the receiving openings 72 are offset with respect to one virtual line parallel to the rotation axis. The amount of the offset is smaller than the distance between the receiving openings 72 and the rotation axis R. This arrangement of the receiving openings 72 with only a small offset to one virtual line parallel to the rotation axis is substantially extending parallel to the rotation axis.

Figure 4E:
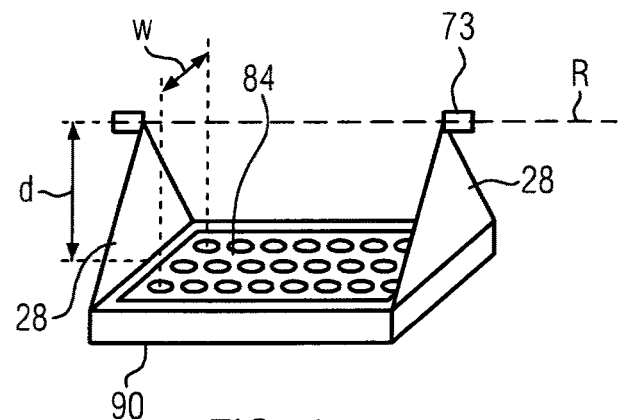

FIG. 4e shows a further embodiment of the sample carrier receptacle 14 having two bearing pins 73 defining the rotation axis R, a frame 90 for holding a microtiter plate 84 and two endwalls 28 for connecting the frame 90 with the bearing pins 73. The width w of the arrangement of the reaction vessels of the microtiter plate 84 in lateral direction to the rotation axis R is significantly smaller than the distance d between the rotation axis R and the microtiter plate 84 inserted into the frame 90. Thus, it is ensured that nearly the same centrifugal force is acting on all samples in the different vessels of the microtiter plate 84.

Figure 5A:
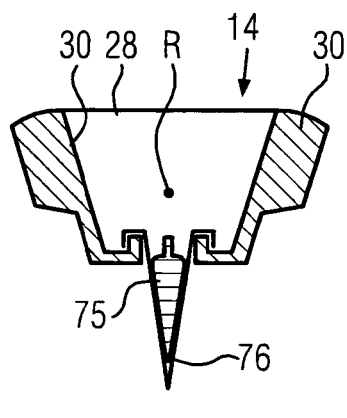
FIG. 5a, 5b show a sample carrier receptacle for holding a blood bag in a cross-section view and a side view.
Figure 5B:
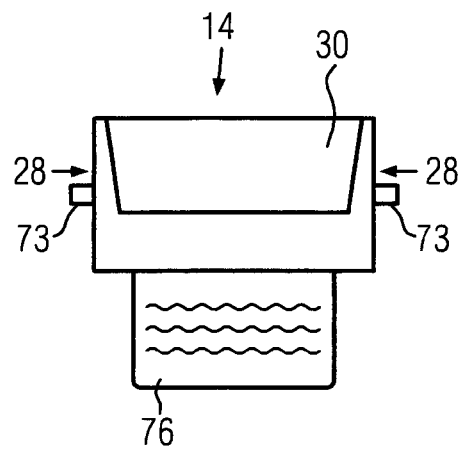

FIG. 5a, 5b show another embodiment of a sample carrier receptacle 14 for holding a blood bag 75. This receptacle 14 again comprises two side walls 30, two end walls 28 and a bottom wall 71 having one receiving opening 72. A rack 76 is provided for holding a blood bag 75. The rack has a collar for engaging with upwardly directed protrusion located at the edge of the receiving opening 72.

The rack is compressible so that after centrifuging the blood bag the rack and the blood bag can be compressed and plasma collected in the upper portion of the blood bag can be squeezed out so that only red blood cells remain in the blood bag.

The rack 76 is a disposable which is only used once.

The side walls 30 are thicker than the corresponding side walls 30 of the above described embodiments, because these side walls 30 are used as counterweight for the blood bag 75. Thus blood bags 75 with a volume of some hundred ml can be fixed to this receptacle and centrifuged with a high rotational speed.

Such a receptacle 14 for centrifuging larger vessels can be preferably provided with an automatically adjustable counterweight. The position of the counterweight can be adjusted by means of an electrical actuator, wherein a rotation with a lower speed the unbalance of the rotating parts is detected and by displacing the counterweight compensated. After having the rotating parts balanced, the rotational speed can be increased.

Figure 6:
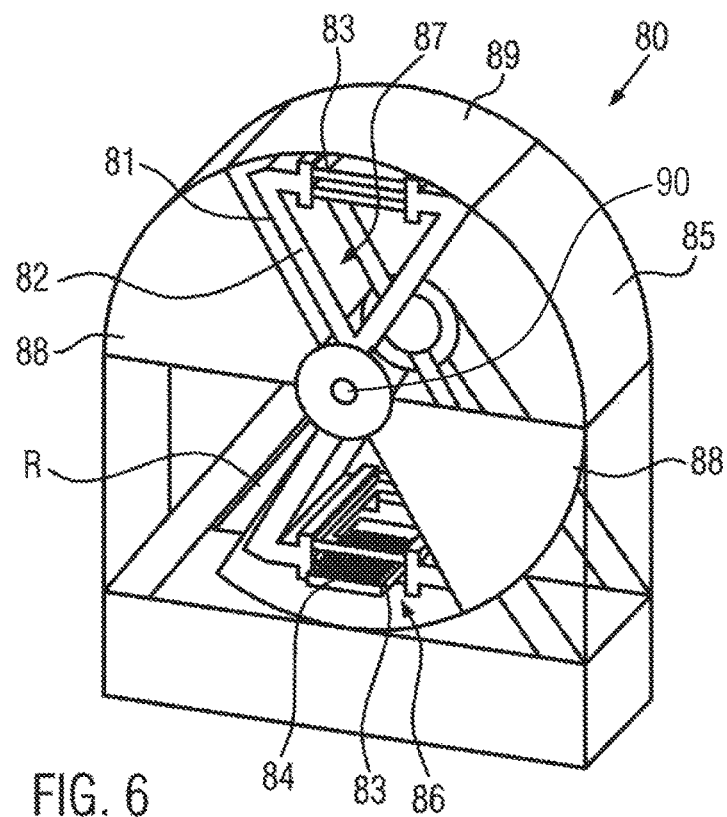
FIG. 6-9 show schematically a further embodiment of a centrifuge for centrifuging microtiter plates in several operational stages.

FIG. 6 shows schematically a further embodiment of a centrifuge 80. The centrifuge 80 comprises a rotor 81, which is rotatable mounted around the horizontal axis R. The rotor 81 comprises a framework 82 in the form of an X, wherein at the outer end of the framework 82 sample carrier receptacles 83 are provided. These receptacles 83 are embodied for taking up a microtiter plate 84. Such a microtiter plates are well known in the art and there are microtiter plates having 96, 384, 1536 vessels.

The centrifuge 80 comprises a housing 85 with a lower opening 86 below the rotational axis R. and an upper opening 87 above the rotational axis R. The openings 86, 87 can be closed by a rotatable door 88. In order to be able to place the rotary drive unit of the sample carrier receptacle as close as possible to the sample carrier receptacle, a bearing point of the sample carrier receptacle can be provided between the holding section and a drive section of the sample carrier receptacle in order to introduce the rotation drive force of a rotation drive unit.

In FIG. 6, the centrifuge 80 is shown in a stage in which one receptacle 83 is placed on the bottom section and the other receptacle 83 is placed on the top section of the centrifuge. Both receptacles 83 are arranged horizontally in this position. A microtiter plate 84 can be loaded into the lower receptacle 83 by means of a horizontal, translational movement.

After loading the centrifuge, the door 88 closes the openings 86, 87 and the rotor is rotated around the rotation axis R. (FIG. 7).

As the centrifuge 80 is loaded or discharged by a horizontal translational movement of the microtiter plate 84, this centrifuge can be easily implemented in an automatic liquid handling system.

Figure 7:
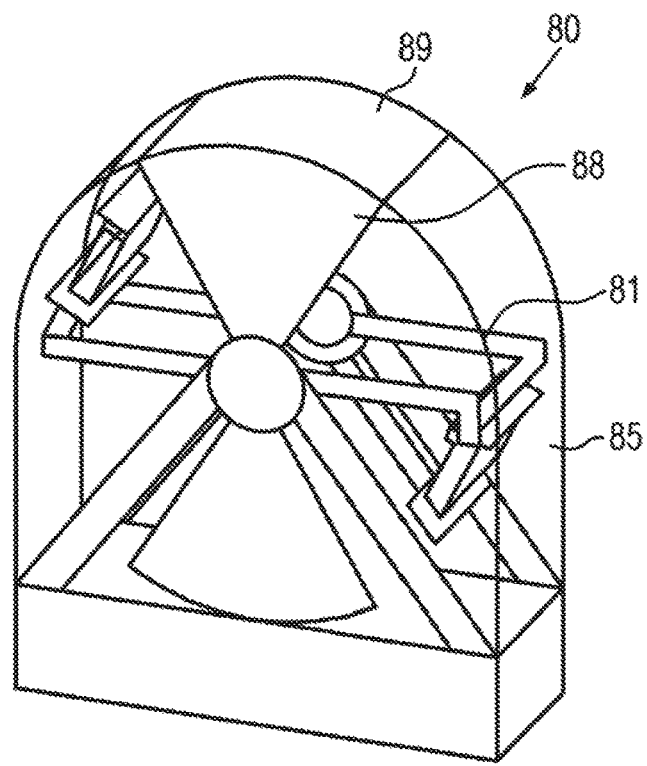
Figure 8:
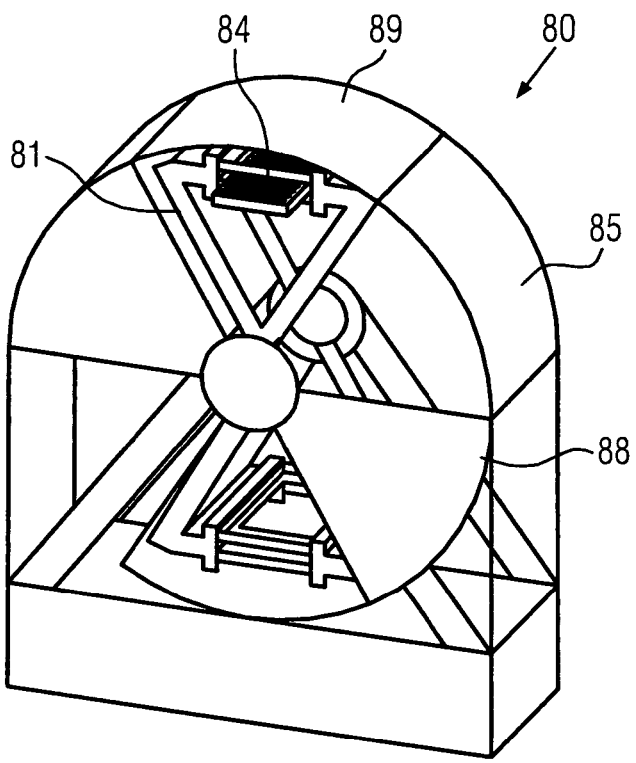
Figure 9:
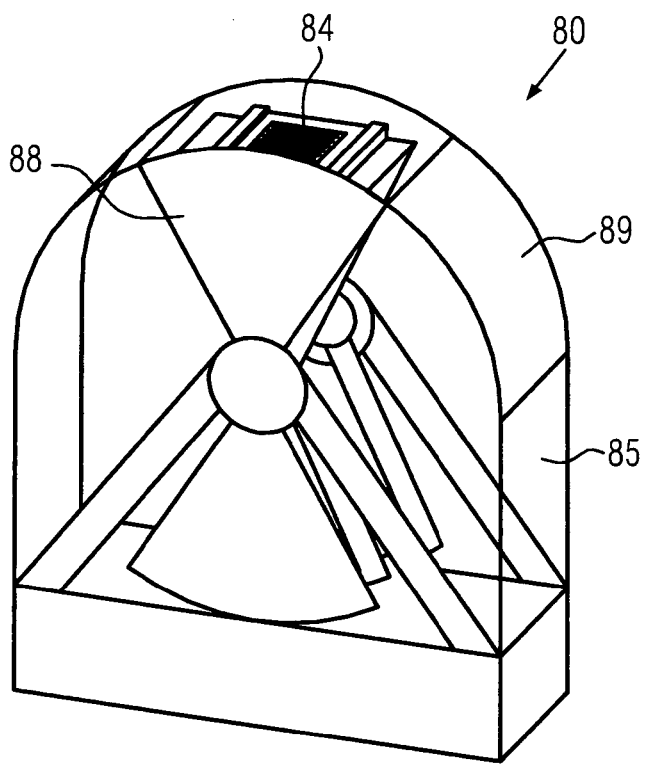

FIG. 8 shows the same centrifuge as in FIGS. 6 and 7, however, the receptacle 83 placed at the upper portion of the centrifuge 80 is loaded with a microtiter plate. The vessels of the microtiter plate 84 are directed with their openings radially outwardly. By rotating the rotor 81, the content of the vessels of the microtiter plate 84 is splashed radially outwardly. This arrangement is used for washing the vessels of a microtiter plate 84. After loading the centrifuge with a microtiter plate 84, the rotor is rotated by 180° and stopped. All liquid content which does not adhere by means of surface tension is dropping out of the vessels into a bowl (not shown) placed below. Then the rotor is rotated with high rotational speed to expel all residual content from the vessels of the microtiter plate.

The housing 85 comprises at the top portion an automatically removable lid 89. The microtiter plate can be held directly below the upper portion of the housing 85 and then the lid 89 can be opened. With the pipetting means a washing solution can be introduced into the vessels of the microtiter plate and the rotation of the microtiter plate can be repeated with the washing solution. This process can be repeated several times. Thus the centrifuge 80 according to the present invention can also be used as a washing station for washing reaction vessels which are used for carrying out chemical and/or biological reactions.

If such a centrifuge shall be used for both washing and centrifuging, then it is preferable to provide the housing 85 with an inner disposable cover, such as a paper-cylinder, which can be replaced after each washing process.

It has been shown that the residual volume of the washing solution, which remained in a vessel after centrifuging a microtiter plate, was smaller than 0.01 µl applying an amount of washing solution of e.g. 200 µl in several washing steps results in a dilution ratio of 20.000:1. Ordinary washing machines for washing microtiter plates provide a dilution ratio of 40:1. Using such a centrifuge increases the dilution ratio 5.000 times. Thus, the washing with a centrifuge improves the efficiency dramatically in comparison to ordinary washing systems for microtiter plates.

Preferably, several washing steps, e.g. two, three or four washing steps, are carried out, wherein each washing step is started with pipetting a washing solution into the vessels. Then the solution is discharged by centrifugation. It is possible to use the same washing solution for all washing steps or also to use different kind of washing solutions for the different washing steps.

The washing solution and/or the vessels which are to be washed can be heated for improving the washing efficiency.

As the washing solution is discharged from the vessels by means of centrifugation, it is not necessary to aspire the washing solution by needles as it is done in the prior art. This often causes problems in prior art devices, because sometimes the needles are blocked by debris contained in the vessels.

The present invention is described above by means of several different examples. Such a centrifuge can be part of an incubator by which a temperature in the range of e.g. −20° C.−+40° C. is adjustable.

Furthermore, such a centrifuge can be coupled to a vacuum pump so that during the centrifuging of samples simultaneously a vacuum can be applied to the housing in which the centrifuge is located. This allows simultaneously the centrifugation and the drying of samples.

Furthermore, it is possible to couple the centrifuge to a source of inert gas so that the centrifuge, which is arranged in a closed housing, is completely covered by the inert gas. Such inert gases are for example $N_2$, $CO_2$, He.

The centrifuge according to FIG. 6-8 can be embodied in that the lid 89 and the door 88 are coupled so that they are opened and closed simultaneously.

The motor for rotating the rotor 81 is preferably a servomotor. When the rotation of the rotor 81 is started, it has to be accelerated very quickly to ensure that no sample is lost at the top position of the vessel in the centrifuge. Therefore, it can be appropriate to start the movement of the rotor by a swinging movement forward and backwards, wherein the amplitude and the speed of the rotor are stepwise increased. Such a swinging motion can also be appropriate to stop the motion of the rotor in that the vessel or microtiter plate, respectively, is moved during the deceleration process through the most bottom position and swings back slowly for being finally completely stopped in the most bottom position of the receptacle 83 of the rotor.

The receptacle 83 of the rotor can be provided with a clamp for clamping a microtiter plate or a rack for holding several separate vessels, particularly tubes. The receptacle 83 can be embodied for taking up different kinds of microtiter plates, particularly microtiter plates comprising deep wells.

Furthermore, a barcode reader can be provided in the bottom portion of the centrifuge to read barcodes provided on the bottom wall of the vessels of a microtiter plate or on the bottom wall of tubes.

The liquid sample can be covered with a layer of oil. Such a layer of oil can be automatically added to the sample by a pippeting means. Such a layer of oil can reliably prevent the liquid sample from coming into contact with the air. In combination with using a centrifuge such a layer of oil can be provided on the bottom of a tube. By centrifugation of a layer of oil and a liquid probe above the oil layer the liquid probe is immersing through the oil layer so that the liquid probe is completely covered by the oil layer. Thus it is possible to firstly fill in an oil layer and afterwards the liquid sample which has to be covered by the oil layer. Thus tubes can be used being initially filled with an oil layer, wherein liquid samples can be immersed through the oil layers. This makes the covering of liquid samples easy to automate, as no lids have to be handled.

In the following examples of using this layer of oil are described for centrifuging samples, reagents and reaction mixes. Samples are aqueous solutions containing a template or target which is to investigate. Reagents contain all components for a certain chemical and/or biological reaction besides the templates. Such chemical and/or biological reactions are typically PCR, BDNA, sequencing or similar reactions. A reaction mix contains both at least one sample and reagents. It is also distinguished between reaction mixes before amplification, which are called pre-reaction mix, and reaction mixes after amplification, which are called post-reaction mix.

Method a

A vessel can be initially provided with a layer of oil. The sample can be put into the vessel by means of pipetting. The vessel containing the sample laying on the layer of oil is centrifuged, whereby the sample is immersing the layer of oil so that after the centrifugation step the sample is covered by the layer of oil.

Method b

A sample is put into a vessel. A layer of oil is put onto the sample. The vessel containing the sample and the layer of oil is centrifuged, wherein potential air between the sample and the layer of oil is expelled.

This is a simple method for avoiding that the sample can come into contact with air.

Method c

Method c is based on either method a or method b and starts with a vessel containing a sample which is covered by a layer of oil.

Reagents suitable for PCR are put into the vessel. The vessel is centrifugated so that the reagents immerse through the layer of oil.

This reaction mix undergoes the temperature cycling of PCR so that the templates or targets contained in the sample are amplified.

Optionally it is possible to add a further reaction mix for carrying out a further chemical and/or biological reaction which is also put under the layer of oil by means of centrifugation.

Thus, the use of a layer of oil for covering a sample makes it possible that the sample comes into contact with reaction mixes without any danger of contamination and several reaction mixes can be added stepwise. The whole process can be carried out just by pipetting and centrifugation. There is no need to mechanically opening a lid or ceiling reaction vessels by means of falls.

The invention claimed is:

1. A sample carrier centrifuge for a sample carrier having a sample carrier receptacle for holding one or more sample carriers, which can be rotated around a rotation axis and has a holding section into which the sample carrier can be inserted in a loading procedure when the sample carrier receptacle is not rotating, in which section the sample carrier is held in the loaded state of the sample carrier receptacle, and from which section the sample carrier can be removed in an unloading procedure,
wherein a platform of the sample carrier centrifuge, which is embodied for supporting the sample carrier centrifuge in accordance with said sample carrier centrifuge's designated use, is oriented parallel to the rotation axis, wherein the sample carrier has at least one sample channel extending along an essentially central sample channel longitudinal axis, wherein the sample carrier receptacle is embodied and situated so that when the sample carrier is accommodated in the holding section of the sample carrier receptacle, the sample channel longitudinal axis of said sample channel is oriented orthogonally to the rotation axis, both when the sample carrier receptacle is rotating and when the sample carrier receptacle is not, and wherein the sample carrier receptacle is mounted to a centrifuge housing at two bearing points spaced along the rotation axis and said sample carrier receptacle is able to rotate around the rotation axis while significantly reducing a tendency of the axis to oscillate at high speeds.

2. The sample carrier centrifuge as recited in claim 1 with the sample carrier, wherein the sample carrier receptacle is embodied for holding several sample carriers which are laterally away from the rotation axis wherein a distance between the sample carriers and the rotation axis is at least as long as the lateral distance of the sample carriers in the sample carrier receptacle.

3. The sample carrier centrifuge as recited in claim 1 with the sample carrier, wherein the sample carrier has at least one sample channel extending along an essentially central sample channel longitudinal axis, wherein the sample carrier receptacle is embodied and situated so that when the sample carrier is accommodated in the holding section of the sample carrier receptacle, the sample channel longitudinal axis of its sample channel is oriented essentially orthogonal to the rotation axis, both when the sample carrier receptacle is rotating and when it is not.

4. The sample carrier centrifuge as recited in claim 3, wherein the sample channel longitudinal axis is spaced radially apart from the rotation axis by a distance that is not greater than the greatest radial dimension of the sample channel in a radial direction that is orthogonal to both the sample channel longitudinal axis and the rotation axis, wherein said greatest radial distance is the distance between the sample channel longitudinal axis and the inner wall of the sample channel.

5. The sample carrier centrifuge as recited in claim 1 with the sample carrier, wherein the axial distance of the sample carrier from the rotation axis in the direction of the sample channel longitudinal axis is less than the dimension of the sample carrier in its axial direction.

6. The sample carrier centrifuge as recited in claim 1, wherein the sample carrier receptacle has two side walls essentially parallel to the rotation axis between which the rotation axis passes and between which the holding section is defined.

7. The sample carrier centrifuge as recited in claim 6, wherein each side wall has a partition wall section for delimiting a receiving opening of the holding section.

8. The sample carrier centrifuge as recited in claim 7, wherein the sample carrier receptacle has a balancing section and the partition wall section is situated closer to the rotation axis than the balancing section.

9. The sample carrier centrifuge as recited in claim 8, wherein said sample carrier centrifuge has as many balancing sections as side walls.

10. The sample carrier centrifuge as recited in claim 8, wherein the partition wall section and the balancing section of a side wall enclose an acute angle.

11. The sample carrier centrifuge as recited in claim 1, wherein said sample carrier centrifuge is balanced in relation to a predetermined sample carrier so that the unloaded sample carrier receptacle rotating around the rotation axis has a greater imbalance than the sample carrier receptacle loaded with the predetermined sample carrier.

12. The sample carrier centrifuge as recited in claim 1, wherein the holding section is provided between the bearing points.

13. The sample carrier centrifuge as recited in claim 12, wherein a bearing point of the sample carrier receptacle is provided between the holding section and a drive section of the sample carrier receptacle in order to introduce the rotation drive force of a rotation drive unit.

14. The sample carrier centrifuge as recited in claim 13, wherein the sample carrier receptacle is embodied as mirror-symmetrical relative to a symmetry plane containing the rotation axis.

15. The sample carrier centrifuge as recited in claim 14, wherein the sample carrier has a plurality of sample channels with respective sample channel longitudinal axes that are parallel to one another.

16. The sample carrier centrifuge as recited in claim 1, wherein the sample carrier receptacle is embodied as mirror-symmetrical relative to a symmetry plane containing the rotation axis.

17. The sample carrier centrifuge as recited in claim 1, wherein the sample carrier has a plurality of sample channels with respective sample channel longitudinal axes that are parallel to one another.

18. The sample carrier centrifuge as recited in claim 17, wherein the sample channel longitudinal axes of all of the sample channels of the sample carrier that can be accommodated on the sample carrier receptacle lie in a common sample carrier plane and the sample carrier plane of a sample carrier is inserted into the sample carrier receptacle contains the rotation axis or is parallel to the rotation axis and spaced apart from the rotation axis by a distance that is not greater than the greatest radial dimension of one sample channel out of the plurality of sample channels of the sample carrier in a radial direction that is essentially orthogonal both to the sample channel longitudinal axis of the sample channel and to the rotation axis, wherein said greatest radial distance is the distance between the sample channel longitudinal axis and the inner wall of the sample channel.

19. The sample carrier centrifuge as recited in claim 1, wherein the sample carrier receptacle is embodied to accommodate exactly one sample carrier.

20. The sample carrier centrifuge as recited in claim 1, wherein said sample carrier centrifuge has a centrifuge housing an access opening that can be closed and opened by means of a cover movably mounted to the centrifuge housing.

21. The sample carrier centrifuge as recited in claim 20, wherein an inner surface of the centrifuge housing oriented toward the sample carrier receptacle and/or an inner surface of the cover oriented toward the sample carrier receptacle—at least along sections of their circumference and preferably along their entire span in the circumference direction around the rotation axis—is/are shaped in the form of a cylinder or partial cylinder, whose cylinder axis is the rotation axis.

22. The sample carrier centrifuge as recited in claim 15, wherein said sample carrier centrifuge has a centrifuge housing with an access opening that can be closed and opened by means of a cover movably mounted to the centrifuge housing.

23. The sample carrier centrifuge as recited in claim 22, wherein an inner surface of the centrifuge housing oriented toward the sample carrier receptacle and/or an inner surface of the cover oriented toward the sample carrier receptacle—at least along sections of their circumference and preferably along their entire span in the circumference direction around the rotation axis—is/are shaped in the form of a cylinder or partial cylinder, whose cylinder axis is the rotation axis.

24. The sample carrier centrifuge as recited in claim 1, wherein said sample carrier centrifuge has a plurality of sample carrier receptacles.

25. The sample carrier centrifuge as recited in claim 24, wherein the rotation axes of the plurality of sample carrier receptacles are essentially situated in one rotation axis plane.

26. The centrifuge apparatus, including a sample carrier centrifuge having an essentially horizontally arranged rotation axis as recited in claim 1 and a pipetting device for automatically dispensing a fluid into a sample channel of the sample carrier held in the at least one sample carrier receptacle; the pipetting device has a pipetting channel extending essentially in the vertical direction.

27. The centrifuge apparatus as recited in claim 1, comprising a loading machine for automated loading and unloading of the at least one sample carrier receptacle.

* * * * *